United States Patent [19]

Ofsthun et al.

[11] Patent Number: 5,240,614
[45] Date of Patent: Aug. 31, 1993

[54] PROCESS FOR REMOVING UNWANTED MATERIALS FROM FLUIDS AND FOR PRODUCING BIOLOGICAL PRODUCTS

[75] Inventors: Normal J. Ofsthun, Rolling Meadows; Lee W. Henderson, Lake Forest; Richard I. Brown, Northbrook; Robin G. Pauley, Ingleside, all of Ill.

[73] Assignee: Baxter International Inc., Deerfield, Ill.

[21] Appl. No.: 818,851

[22] Filed: Jan. 10, 1992

[51] Int. Cl.⁵ .............................. B01D 61/28
[52] U.S. Cl. .................. 210/645; 210/500.23; 210/500.41
[58] Field of Search ....... 210/500.41, 500.23, 210/644, 645; 264/41, 209.1

[56] References Cited

U.S. PATENT DOCUMENTS

| | | | |
|---|---|---|---|
| 4,230,463 | 10/1980 | Henis et al. | 55/16 |
| 4,276,172 | 6/1981 | Henne et al. | 210/490 |
| 4,286,015 | 8/1981 | Yoshida et al. | 428/305 |
| 4,351,860 | 9/1992 | Yoshida et al. | 427/246 |
| 4,610,791 | 9/1986 | Henne et al. | 210/490 |
| 4,802,942 | 2/1989 | Takemura et al. | 55/16 X |
| 4,822,489 | 4/1989 | Nohmi et al. | 210/500.23 |
| 4,874,522 | 10/1989 | Okamoto et al. | 210/321.6 X |
| 4,882,223 | 11/1989 | Aptel et al. | 428/398 |
| 4,983,293 | 1/1991 | Yoshida et al. | 210/500.23 |
| 5,015,585 | 5/1991 | Robinson | 210/636 X |
| 5,049,276 | 9/1991 | Sasaki | 210/500.23 |

FOREIGN PATENT DOCUMENTS

| | | |
|---|---|---|
| 60-246812 | 12/1985 | Japan. |
| 61-164602 | 7/1986 | Japan. |
| 62-117812 | 5/1987 | Japan. |
| 62-241528 | 9/1990 | Japan. |

Primary Examiner—Frank Spear
Attorney, Agent, or Firm—Charles R. Mattenson; Allan O. Maki

[57] ABSTRACT

The invention employs dual-skinned membranes useful as one way or rectifying membranes which reduce back filtration of solute molecules in dialysis and which improve nutrient supply and product recovery in membrane bioreactors. The membranes are dual-skinned polymeric materials preferably in the form of hollow fibers. The membranes have sieving coefficient characteristics different for flow of liquids in one direction from that in the opposite direction. Improved dialysis devices are formed by using bundles of the hollow fiber membranes as a dialysis means having rectifying properties. Improved bioreactors are formed by using bundles of hollow fiber as a growth vessel having rectifying properties.

7 Claims, 2 Drawing Sheets

PROCESS FOR REMOVING UNWANTED MATERIALS FROM FLUIDS AND FOR PRODUCING BIOLOGICAL PRODUCTS

FIELD OF THE INVENTION

This invention relates to fluid filtration devices, such as blood dialysis devices, bioreactors, and methods pertaining thereto. More specifically, the invention relates to an improved dialysis device or bioreactor having rectifying filtration properties, dual-skinned membranes for performance of such dialysis and other filtration procedures, and methods for using such membranes.

BACKGROUND OF THE INVENTION

Dialysis membranes and devices perform important life sustaining functions when used in artificial kidneys and other types of filtration devices. A well recognized problem of high flux dialyzers is the back filtration from dialysate to the blood of undesirable molecules. Due to the high cost of using sterile, pyrogen-free dialysates, it would be highly desirable to have available a dialysis membrane which could remove relatively large solutes such as $\beta$-2 microglobulin while preventing passage of similarly sized molecules from dialysate to blood. Membranes, however, which offer a high rate of diffusion of solutes from the blood to dialysate also suffer from high rates of back diffusion of solutes from dialysate back to the blood. Similarly, existing membranes which offer a high rate of convection also suffer from high rates of back filtration. A need has therefore existed for dialysis membranes which provide for adequate removal of uremic toxins from the blood while preventing back transport of undesirable substances to the blood. Similarly, other fluid filtration processes benefit from the availability of membranes having such rectifying properties.

A need has also existed for devices such as bioreactors in which rectifying membranes provide a means for simultaneously supplying nutrients to and carrying products and waste byproducts from live cells that are used to make products which cannot be economically produced by traditional synthetic chemistry techniques.

BRIEF SUMMARY OF THE INVENTION

An important object of the invention is to provide new and improved processes membranes utilizing in filtration devices such as dialysis devices. A further aspect of the invention is to provide improved filtration method using filtration devices containing membranes with rectifying properties, i.e., have a greater sieving coefficient in one direction than the other.

A further important aspect of the present invention involves use of dual-skinned membranes such as hollow fibers in which the pore size and structure, and the resulting sieving coefficient, differs between the two opposed surfaces of the membrane. In the preferred embodiment, the membranes are in the shape of hollow fibers in which the sieving coefficient, or permeability to molecules of a particular size, of the inner wall or skin of the fiber is greater than that of the outer wall. Such fibers can be assembled into dialysis devices in accordance with known procedures to provide such dialysis devices in which large solutes can be removed from a fluid, such as blood, flowing within the interior of the fibers to a filtrate or dialysate liquid which surrounds the fibers. Since a tighter or less permeable skin is provided on the outside of the fibers, it has been found that back transport from the outside of the fibers to the inside is substantially reduced.

Another important object of the invention relates to use of dual-skinned membranes useful in dialysis as one way or rectifying membranes which reduce back filtration. The preferred membranes are dual-skinned polymeric materials preferably in the form of hollow fibers. The membranes have skins of polymer on their opposite sides with differing solute permeability or sieving coefficient characteristics. Such membranes can be formed by extruding a polymer dissolved in a solvent while contacting at least one surface with a non-solvent for the polymer that is miscible with the solvent. The other surface is also contacted with a non-solvent, but one which is either different from the first non-solvent or which contains a soluble additive that changes the pore size and structure of the skin formed on the dissolved extruded polymer.

In another aspect of the invention improved dialysis devices having rectifying properties are formed by using the membranes provided by the invention. In a further aspect of the invention there is provided a method of making a dual-skinned membrane which includes the steps of providing a solution of a polymer in a solvent liquid, extruding the solution to form a continuous elongated shape (for example, a hollow tube) having a thin cross-section of generally uniform thickness and opposed broad surfaces, contacting one of the surfaces with a first liquid that is miscible with said solvent, but is a non-solvent for said polymer, to form a polymeric skin on said surface. The opposite surface is either simultaneously or subsequently contacted with a second liquid non-solvent for said polymer. The second non-solvent liquid is also miscible with the solvent and causes a second polymeric skin having different permeability characteristics from that of the first polymeric skin to be formed on the opposite surface of the membrane.

In accordance with a still further aspect of the invention, rectifying membranes are incorporated into bioreactors to provide such devices in which transport across the membrane to the reaction vessel occurs at a different rate than does transport back across the membrane from the vessel to a fluid stream used to supply nutrients and to carry away waste by-products from live cells contained in the vessel. Use of such membranes allows costly serum components to pass through the membranes to the cells and then be concentrated in the reaction vessel, thereby reducing the quantity of the serum components required. The hollow fiber membrane bioreactors of this invention are dialysis-like devices in which live animal, plant or bacterial cells are grown in the shell space that surrounds the hollow fibers. The fluid flowing through the fibers acts both to supply nutrients to the cells and to remove waste products. There is, in such case, no direct fluid flow through the shell area, the ports leading to the shell space being closed to provide the vessel for the bioreactor. However, Starling's flow within the bioreactor carries solutes in and out of the shell space. Depending on the size of the product, it may pass back through the membrane and be purified from the waste stream, or it may collect in the shell space and be removed therefrom on a batch or semi-continuous basis.

In the preferred embodiment of the method a continuous hollow cylinder is formed by extrusion around a core of non-solvent thereby forming a skin on the interior of the cylinder. A second skin is formed on the exterior by contacting it with the second non-solvent. A bundle of the resultant hollow cylinders or fibers can be used to form a dialysis device. Preferably one of the non-solvents is an aqueous solution that contains a solute which increases the porosity of the first, inner, skin. The outer surfaces of the hollow fibers can be contacted with a different non-solvent composition to form a second skin having different solute permeability characteristics.

The preferred dialysis devices of the invention are formed from hollow polymeric fiber membranes having a microporous structure within the walls thereof, with the microporous structure having a skin of polymer formed integrally with the interior and exterior surfaces thereof. The exterior skin has a sieving coefficient different from that of the internal skin. The rectifying dialysis devices of the invention provide a means for removing unwanted material from bodily fluids such as blood in which a high rate of filtration of solutes from blood to dialysate is offered, while a substantially lower rate of back filtration of undesired solutes from dialysate to blood is maintained.

DRAWINGS

The invention will be further explained in the following detailed description and with reference to the accompanying drawings, wherein.

Figure 1:
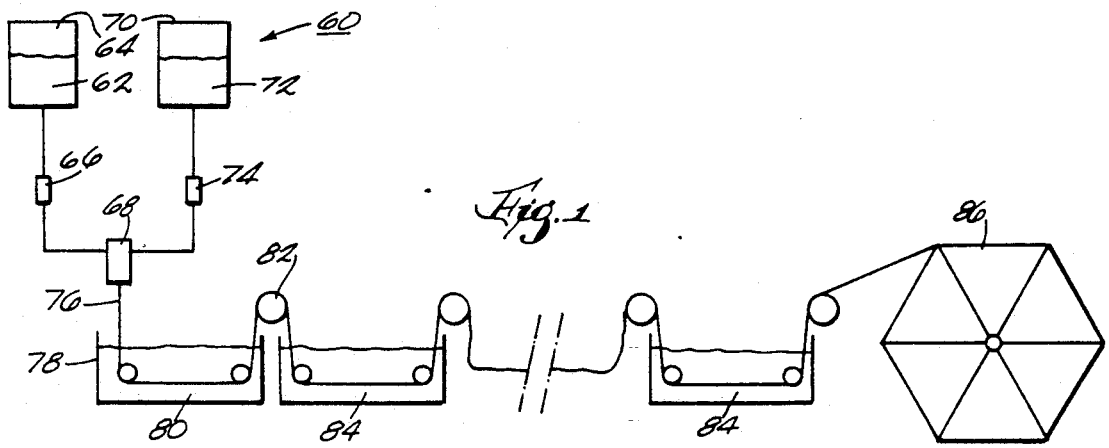
FIG. 1 is a diagrammatic view illustrating the process for forming membranes of the invention in hollow fiber form.

Referring more specifically to the drawings, FIG. 1 diagrammatically illustrates a hollow fiber spinning system 60. A solution 62 of a polymer in an organic solvent is contained in vessel 64 from where it is pumped to an annular extrusion die 68 by means of a metering pump 66. Similarly, a coagulant solution 72 which is a non-solvent for the polymer is contained in a second vessel 70 and is transferred to die 68 by means of another pump 74.

The interaction of non-solvent 72 and the polymer solution 62 at the interface 63 formed as the solutions exit the die in contact with each other determined the ultimate structure and properties of the inner membrane.

The formed extrudate then falls through an air gap 76 and enters a bath 78 containing a second non-solvent coagulant solution 80. The interaction of the extrudate with the second solution 80 determines the structure and properties of the outer membrane. The fiber is pulled through bath 78 by means of driver roller 82 and through one or more additional baths 84, as required, to completely extract the solvent from hollow fibers. The extracted fiber is finally taken up onto a multi-segment winder 86 and allowed to dry.

Dried fibers 88 are cut to length and placed in a housing 90. The fibers 88 are sealed in the housing by means of a thermosetting resin 92. The assembly is fitted with end caps 94 and 96. An inlet 97 and outlet 98 for filtrate liquid are also provided on the housing.

Figure 5:
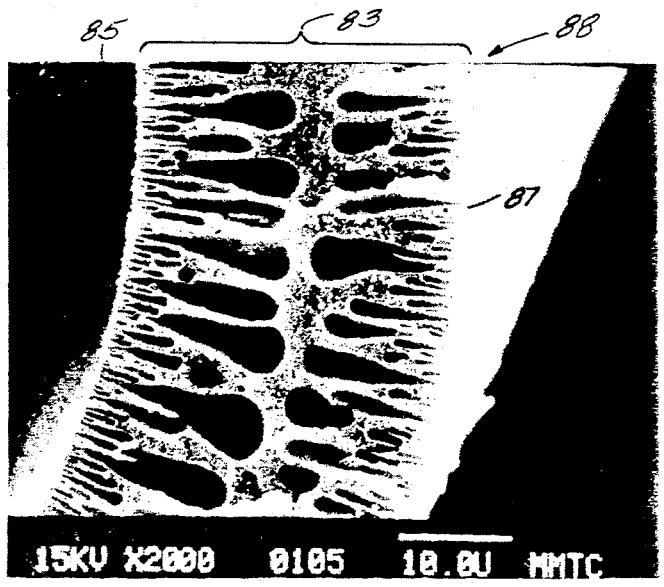
FIGS. 5 and 6 are cross-sectional views of a hollow fiber membrane of the invention of different magnifications taken with an electron microscope; and, FIG. 7 is a side elevational view of a bioreactor device in accordance with the invention.
Figure 6:
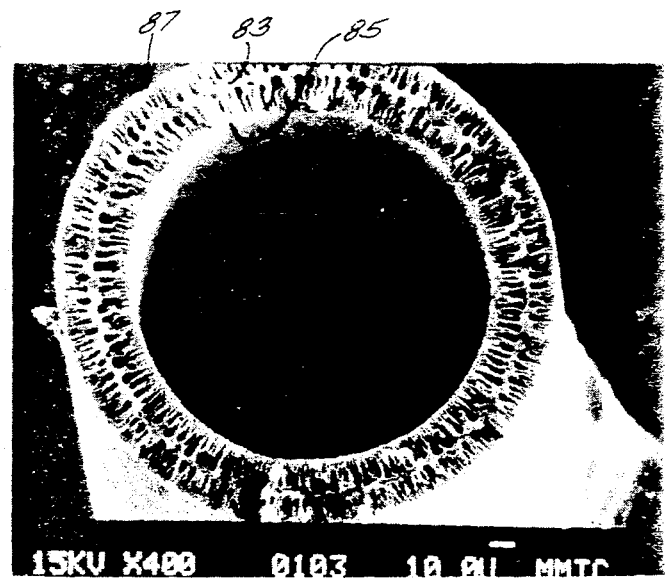

FIG. 5 and 6 illustrate in magnified cross-section a typical fiber 88 of the invention showing internal microporous structure 83, an inner skin 85 and an outer skin 87 having different porosity than inner skin 85.

The overall sieving coefficient is the fraction of the incoming solute that passes through the membrane along with the fluid that is being filtered. It is calculated by dividing the concentration of solute on the downstream side of the membrane by its concentration on the upstream side of the membrane.

For a single-skinned membrane, the overall sieving coefficient is equal to the sieving coefficient of the skin, which is the fraction of solute that passes through that skin. The sieving coefficient of the skin itself depends only on the relative sizes of the pore and the solute molecule. The tighter the skin (i.e. smaller the pores), the smaller the fraction of a given molecule which will pass through it.

However, for a dual-skinned membrane, the concentration of solute which reaches the second skin depends on the characteristics of the first skin as well as the flow conditions, so the overall sieving coefficient is a property of both flow and membrane properties. The key to the rectifying membrane, in which the sieving coefficient in one direction is different from the sieving coefficient in the other direction, is that flow in one direction results in buildup of solute within the two skins of the membrane.

Figure 4:
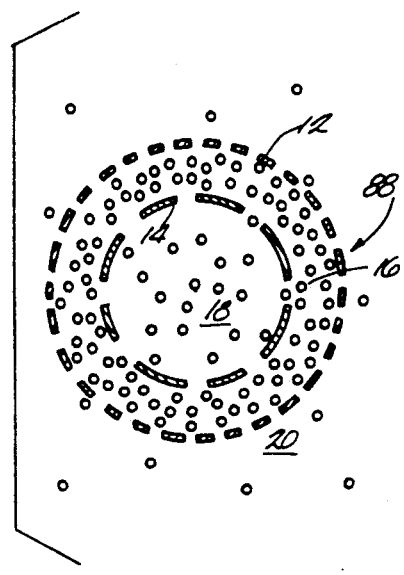
FIG. 4 is a sketch in greatly enlarged scale illustrating, hypothetically, the mechanism of filtration that occurs in use of the filtration devices of the invention.

FIG. 4 is a schematic of a dual-skinned rectifying membrane 88 in which the outer skin 12 is tighter than the inside skin 14 and fluid is passing from the inside to the outside as a result of an imposed pressure gradient. In this case, some of the molecules which enter the central area 16 of membrane 88 become trapped when they reach the tighter outer skin 12. The concentration inside the membrane goes up until it reaches a steady state value, and the resulting concentration in the fluid 20 outside the fiber goes up along with it. The concentration in the fiber lumen 18 has not changed, so the overall sieving coefficient increases with time until it reaches a steady-state value that is higher than would be obtained with the tight skin 12 alone.

If that same membrane is exposed to a pressure gradient from the opposite direction, with flow from the outside to the inside, the solute has a hard time getting into the membrane at all, so there is no buildup in the membrane. In this case both the concentration within the membrane and the concentration on the downstream side of the membrane are low, and the overall sieving coefficient is smaller than that which was obtained in the other direction.

Various polymers can be employed in the process of the invention to form hollow fibers. The polymers must be soluble in at least one organic solvent and insoluble in another liquid that is miscible with the solvent. Examples of suitable polymers are polysulfone, polyacrylonitrile, polyamide, polyvinylidene diflouride, polypropylene, and polyethersulfone. Illustrative examples of solvents for such polymers include N-methyl-2-pyrrolidone, N,N'-dimethylformamide, N,N'-dimethylacetamide and γbutyrolactone. The preferred non-solvent which can be used as a coagulation or gelation agent for formation of the skins is water. Other suitable liquids include methanol, ethanol-water mixtures such as 95 or 99.5 vol % ethanol in water, or isopropyl alcohol. Various materials can be added to the non-solvents to form skins of differing porosities. Examples include polyvinyl alcohol, Tetra-ethylene-glycol, poly-ethylene-glycol, perchlorate salts, and polyvinyl pyrrolidone.

An important advantage of the present invention is the ability to provide fibers having different sieving coefficients for molecules to be filtered out of a liquid which have narrowly defined molecular weight ranges. For example, fibers can be provided that have the ability to filter molecules in the range of 5000 to 10,000 differently from one side of the membrane than the other. By appropriate modification of the porosity, the sieving coefficient differential can also be optimized for molecules having a molecular weight range of 10,000 to 15,000 or even 15,000 to 20,000. Optimization is achieved by adjusting the composition of the coagulant solution and the amount and type of dopants added, as well as by varying the spinning conditions such as flow rate, line speed and gap distance.

EXAMPLES

The following examples illustrate preferred processes for producing and using membranes in accordance with the invention. All parts are given by weight unless otherwise indicated.

Example 1

Figure 2:
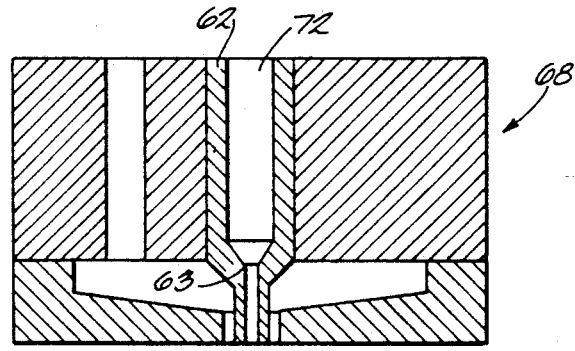
FIG. 2 is a cross-sectional view of an annular extrusion die used in the practice of the invention.

Hollow fibers were prepared using the spinning system and processes described in FIGS. 1 and 2 under the formulation and process conditions shown in Table 1. The fibers were assembled into test modules in accordance with Example 3 and the sieving coefficients determined in accordance with the procedure set forth therein. The sieving coefficients of the resulting fibers for myoglobin were found to be 0.35 when filtrate flow was directed radially outwardly and 0.80 when filtrate flow was inward.

TABLE I

| | |
|---|---|
| Polymer | Polysulfone |
| Solvent | N-methylpyrolidone |
| Spinning Solution Concentration | 15 g/100 g |
| Core Fluid Composition | 15/85 2-propanol/water |
| Precipitation Bath Composition | 2/98 2-propanol/water |
| Wash Baths Composition | Water |
| Gap Distance | 1 cm |
| Line Speed | 18 meters/min |
| Spinning Solution Flow Rate | 1.8 cc/min |
| Core Fluid Pin Diameter | 0.009 inches |
| Die Annular Gap | 0.0035 inches |

Example 2

Hollow fibers were prepared as in Example 1 except that the core fluid composition was 10/90 2-propanol/water and that of the precipitation bath was 5/95 2-propanol/water. FIGS. 5 and 6 are scanning electron micrographs of the resulting fiber in cross-section taken at 2000 times magnification and 400 times magnification, respectively, showing the finger-like structures extending from each boundary and meeting in the middle wall. Sieving coefficients for myoglobin were found to be 0.45 for outward filtrate and 0.90 for inward flow.

Example 3

Test Procedure

Test modules were assembled by potting 100 fibers in mini-dialyzer cases with a length of about 22 cm and an internal diameter of about 0.6 cm. Polyurethane potting extended approximately 1 cm from each header, leaving an active length of about 20 cm. Dialysate ports were located approximately 1 cm from the potting material at each end.

Standard dialysate of the following composition was prepared from concentrate using a hemodialysis machine proportioning system:

| | |
|---|---|
| sodium | 134 mEq/l |
| potassium | 2.6 mEq/l |
| calcium | 2.5 mEq/l |
| magnesium | 1.5 mEq/l |
| chloride | 104 mEq/l |
| acetate | 36.6 mEq/l |
| dextrose | 2500 mEq/l |

Myoglobin solution was prepared by adding the 330 mg of myoglobin per liter of dialysate. Myoglobin (molecular weight = 17,000) is used as a marker for middle molecules such as B-2 microglobulin (molecular weight = 12,000) because it can be measured spectrophotometrically.

The lumen and filtrate compartments were primed with alcohol (isopropanol or ethanol) using a syringe. The test module was then rinsed with excess dialysate, pumping 250 ml through lumen with filtrate port closed and then 200 ml more with one filtrate port open. To measure inlet flow rate, the dialysate ports were closed, the infusion pump was set to the desired speed (10.5 ml/min), outflow was determined by timed collection.

For the sieving coefficient measurement, the test module was clamped in a vertical position, with fibers perpendicular to the table top. An infusion pump was connected to an inlet reservoir, and tubing from the infusion pump was connected to the bottom header. Tubing to waste was connected to the top header. The dialysate ports were closed, the pump was started, and the time at which the test solution reached the device was denoted as time zero.

At time zero, the dialysate side was drained of priming solution by opening both dialysate stopcocks. The lower dialysate port was then closed, and the time zero filtrate sample was taken from the upper port as soon as the filtrate compartment was filled. At the same time, the outlet lumen sample was collected into another beaker. Inlet lumen samples were taken directly from the inlet reservoir. Subsequent filtrate samples were collected at 3 minute intervals, with no loss of filtrate between samples. All samples were measured for myoglobin content using a Gilford spectrophotometer. The sieving coefficient was calculated using the following equation:

$$S = \frac{2 \times \text{concentration in dialysate}}{(\text{inlet lumen concentration} + \text{outlet lumen concentration})}$$

Sampling was continued until the calculated sieving coefficient was constant for 3 consecutive samples.

Figure 3:
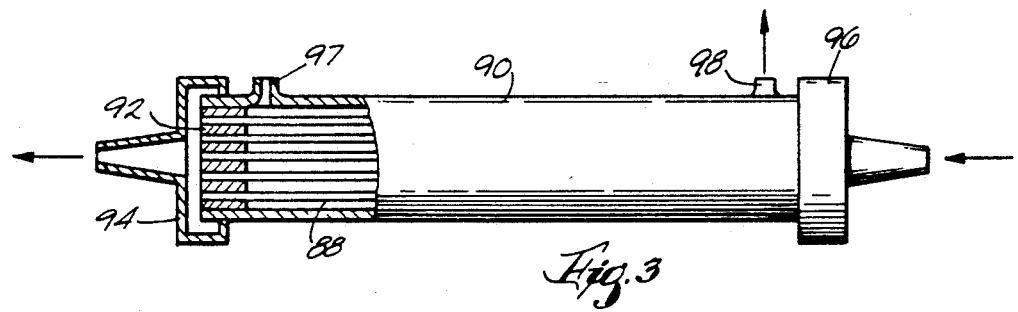
FIG. 3 is a side elevational view with portions in cross-section of a filtration device of the present invention.
Figure 7:
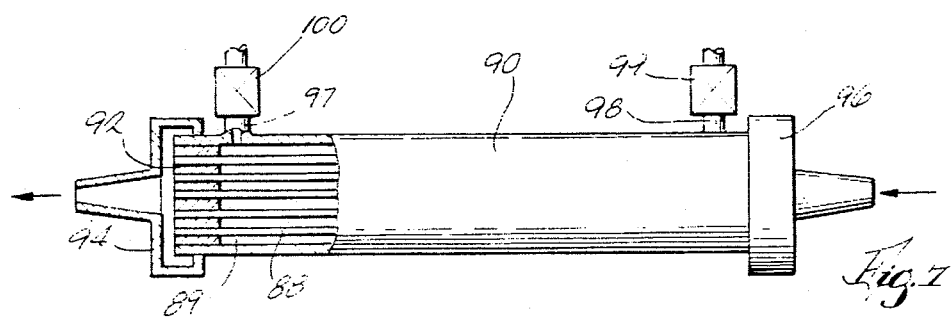

A bioreactor of the present invention is shown in FIG. 7 and consists of a device somewhat similar to the dialysis device shown in FIG. 3. In this case, however, the space 89 surrounding the fibers and enclosed by the interior of housing 90 and thermosetting resin 92 forms a reaction vessel for growth of living cells. Ports 97 and 98 are either omitted or can be closed by means of valves 99 and 100 as indicated. Depending on its size, the product may pass back through the membranes 88 and be purified from the waste stream or it may collect in the shell space which constitutes the reaction vessel from which it may be removed on either a semi-continuous or batch basis.

Transport of nutrients, waste products and desired biological products across the membrane may be by diffusion and/or convection. The axial pressure drop which occurs within the hollow fibers leads to Starling's flow, with convection from the tube side to the shell side at the device inlet and convection from the shell side to the tube side at the device outlet.

Some types of cells require expensive growth media which may contain 10% bovine fetal calf serum. Use of a rectifying membrane allows serum components to pass through the membranes to the cells and then be concentrated in the shell space, thereby reducing the volume of media required. This also reduces the cost of purifying products which pass through the membrane because the volume of the purification stream is smaller.

Rectifying membranes can also be used to concentrate products directly. If the desired product is formed of molecules that are larger than the metabolic waste products as well as the nutrients, the rectifying membrane device can be used to concentrate the products in the shell space while allowing nutrients to reach the cells and waste products to be washed away by the fluid stream passing through the interiors of the hollow fiber membranes.

What is claimed is:

1. A bioreactor comprising a plurality of dual-skinned hollow polymeric membranes having a microporous structure between the walls thereof, said microporous structure having a skin of polymer formed integrally with the interior and exterior surfaces thereof, the microporous structure containing pores capable of retaining solutes in a molecular weight range of about 5000 to 20000 in an increased concentration between the interior and exterior skins, the membrane having an overall sieving coefficient for passage therethrough in one direction of fluids containing solutes comprising molecules in said molecular weight range different from the overall sieving coefficient for passage of such fluids in the opposite direction, said hollow polmeric membranes being secured in a generally parallel orientation in an enclosure, the opposite ends of said enclosure being formed by a polymeric resin which envelopes the exteriors of said fibers, the opposite ends of said fibers extending through said polymeric resin, the exteriors of said fibers and the interior of said enclosure defining a bioreaction vessel for the growth of living cells, inflow means for a fluid which is in fluid flow communication with the interiors of said membranes, outflow means in fluid flow communication with the other ends of said membranes for outflow of said fluid, an opening, normally closed, for introduction and removal of fluids from the interior of said vessel.

2. A device according to claim 1 wherein said fibers comprise a polysulfone polymer.

3. A method of removing unwanted material from a bodily fluid comprising providing a dialysis device comprising a plurality of dual-skinned hollow polymeric membranes secured in a generally parallel orientation in an enclosure, the opposite ends of said enclosure being formed by a polymeric resin which envelopes the exteriors of said fibers, the opposite ends of said fibers extending through said polymeric resin, inflow means for a liquid subjected to dialysis, said inflow means being in fluid flow communication with the interiors of said membranes, and outflow means in fluid flow communication with the other ends of said membranes for outflow of the liquid after dialysis, said dual-skinned hollow polymeric membranes having a microporous structure within the walls thereof, said microporous structure having a skin of polymer formed integrally with the interior and exterior surfaces thereof, the membranes having a sieving coefficient for passage therethrough of liquids containing solutes in one direction that is different than that for the passage therethrough of the same fluids in the opposite direction, a second fluid flow path comprising inflow and outflow passages in fluid flow communication with the interior of said enclosure whereby a dialysis liquid can be caused to flow in contact with the exterior surfaces of said membranes, causing a fluid subjected to dialysis to flow through said fibers, causing a dialysis liquid to flow through said enclosure in contact with the exteriors of said fibers, whereby unwanted matter is removed from said fluid, and back-transport of unwanted matter from the dialysis liquid to said fluid is minimized.

4. A method of removing unwanted material of a defined range of molecular weights from a liquid comprising providing a filtration device comprising a plurality of dual-skinned hollow polymeric membranes secured in a generally parallel orientation in an enclosure, the opposite ends of said enclosure being formed by a polymeric resin which envelopes the exteriors of said fibers with the opposite ends of said fibers extending through said polymeric resin, inflow means for a liquid subjected to filtration, said inflow means being in fluid flow communication with the interiors of said membranes, and outflow means in fluid flow communication with the other ends of said membranes for outflow of the liquid after filtration, said dual-skinned hollow polymeric membranes having a microporous structure within the walls thereof, said microporous structure having a skin of polymer formed integrally with the interior and exterior surfaces thereof, the membranes having a sieving coefficient for passage therethrough of liquids containing solutes in one direction that is different than that for the passage therethrough of the same fluids in the opposite direction.

causing a liquid subjected to filtration to flow through said fibers, causing a second liquid to flow through said enclosure in contact with the exteriors of said fibers, whereby unwanted matter is removed from said liquid, and backflow of unwanted matter of the defined molecular weight range from the second liquid to said filtered liquid is minimized.

5. A method according to claim 4 wherein said molecular weight range is selected from the group of ranges consisting of 5000 to 10,000; 10,000 to 15,000; and 15,000 to 20,000.

6. A method according to claim 4 wherein the filtered liquid is human blood and the unwanted material removed therefrom is $\beta$-2-microglobulin or other middle molecules.

7. A method of producing biological products comprising confining living cells in a bioreactor vessel comprising a plurality of dual-skinned hollow polymeric membranes having a microporous structure between the walls thereof, said microporous structure having a skin of polymer formed integrally with the interior and exterior surfaces thereof, the microporous structure containing pores capable of retaining solutes in a molecular weight range of about 5000 to 20000 in an increased concentration between the interior and exterior skins, the membrane having an overall sieving coefficient for passage therethrough in one direction of fluids containing solutes comprising molecules in said molecular weight range different from the overall sieving coefficient for passage of such fluids in the opposite direction, said hollow polymeric membranes being secured in a generally parallel orientation in an enclosure, the opposite ends of said enclosure being formed by a polymeric resin which envelopes the exteriors of said fibers, the opposite ends of said fibers extending through said polymeric resin, the exteriors of said fibers and the interior of said enclosure defining a bioreaction vessel for the growth of living cells, inflow means for a fluid which is in fluid flow communication with the interiors of said membranes, outflow means in fluid flow communication with the other ends of said membranes for outflow of said fluid, an opening, normally closed, for introduction and removal of fluids from the interior of said vessel, causing a fluid containing nutrients for said cells to flow through said hollow membranes to allow transport of said nutrients through said membrane to said cells, removing waste materials from said cells as they are transferred through said membrane to said fluid, and, subsequently, removing a biological product from said vessel.

* * * * *